United States Patent
Kobayashi (10) Patent No.: US 10,302,635 B2
(45) Date of Patent: May 28, 2019

(54) TESTING DEVICE, TRANSFER MEMBER, METHOD FOR FABRICATING TESTING DEVICE, AND TESTING METHOD

(71) Applicant: Rie Kobayashi, Shizuoka (JP)

(72) Inventor: Rie Kobayashi, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 389 days.

(21) Appl. No.: 15/022,354

(22) PCT Filed: Sep. 19, 2014

(86) PCT No.: PCT/JP2014/075764
§ 371 (c)(1),
(2) Date: Mar. 16, 2016

(87) PCT Pub. No.: WO2015/041372
PCT Pub. Date: Mar. 26, 2015

(65) Prior Publication Data
US 2016/0223535 A1    Aug. 4, 2016

(30) Foreign Application Priority Data

Sep. 19, 2013  (JP) ................................ 2013-194511
Sep. 8, 2014   (JP) ................................ 2014-181888

(51) Int. Cl.
| | | |
|---|---|---|
| *G01N 33/531* | (2006.01) | |
| *G01N 33/543* | (2006.01) | |
| *G01N 33/545* | (2006.01) | |
| *G01N 33/558* | (2006.01) | |
| *B01L 3/00* | (2006.01) | |
| *B05D 5/00* | (2006.01) | |
| *B01D 15/38* | (2006.01) | |
| *G01N 21/78* | (2006.01) | |

(52) U.S. Cl.
CPC ... *G01N 33/54366* (2013.01); *B01D 15/3809* (2013.01); *B01L 3/5023* (2013.01); *B01L 3/52* (2013.01); *B05D 5/00* (2013.01); *G01N 21/78* (2013.01); *G01N 33/531* (2013.01); *G01N 33/545* (2013.01); *G01N 33/558* (2013.01); *B01L 2200/12* (2013.01); *B01L 2200/16* (2013.01); *B01L 2300/044* (2013.01); *B01L 2300/0825* (2013.01); *B01L 2300/0887* (2013.01); *B01L 2300/165* (2013.01); *B05D 2201/02* (2013.01)

(58) Field of Classification Search
None
See application file for complete search history.

(56) References Cited

U.S. PATENT DOCUMENTS

| | | | | |
|---|---|---|---|---|
| 5,013,669 A | * | 5/1991 | Peters, Jr. ........ | G01N 33/54306 435/7.1 |
| 5,266,460 A | * | 11/1993 | Sudo ................ | G01N 33/54386 422/421 |
| 6,872,576 B1 | * | 3/2005 | McIntyre ......... | G01N 33/54306 424/419 |
| 2009/0114845 A1 | | 5/2009 | Nahm et al. | |
| 2012/0177543 A1 | | 7/2012 | Battrell et al. | |
| 2012/0301893 A1 | | 11/2012 | Siciliano et al. | |

FOREIGN PATENT DOCUMENTS

| | | |
|---|---|---|
| JP | 02-038971 | 2/1990 |
| JP | 2007-255999 | 10/2007 |
| JP | 2009-264879 | 11/2009 |
| JP | 2015-007604 | 1/2015 |

OTHER PUBLICATIONS

IUPAC Compendium of Chemical Terminology, definition of "lyophilic", 2014, retrieved from http://dx.doi.org/10.1351/goldbook.L03655 on Jul. 14, 2018, one page (Year: 2014).*
Extended European Search Report dated Aug. 22, 2016 in European Patent Application No. 14846637.8.
International Search Report dated Jan. 13, 2015 for counterpart International Patent Application No. PCT/JP2014/075764 filed Sep. 19, 2014.

* cited by examiner

*Primary Examiner* — Christine Foster
(74) *Attorney, Agent, or Firm* — Oblon, McClelland, Maier & Neustadt, L.L.P.

(57) ABSTRACT

Provided is a testing device including a flow path in which an analyte is flowed, wherein a composition containing a reagent reactive with the analyte and a lyophilic resin is placed at one position or a plurality of positions of the flow path.

9 Claims, 3 Drawing Sheets

TESTING DEVICE, TRANSFER MEMBER, METHOD FOR FABRICATING TESTING DEVICE, AND TESTING METHOD

TECHNICAL FIELD

The present invention relates to a testing device in which a reagent for detecting an analyte is placed.

BACKGROUND ART

Conventionally, fluidic devices having a flow path have been used in order to perform various operations such as separation, mixing, and an analysis of a liquid. A reagent for detecting an analyte can be placed in the flow path of the fluidic devices. Therefore, fluidic devices can be used as testing devices such as biochemical sensors for blood testing or DNA testing, and chemical sensors for quality control of foods or beverages.

In a conventional manner for placing a reagent in the flow path, a solution containing the reagent has been dropped into the flow path. For example, there is disclosed a method of dropping a solution containing a biomaterial, which is a reagent, into a spreading strip formed of nitrocellulose, which is a flow path member (see PTL 1). However, if the dropped reagent solution is spread through the spreading strip by a capillary action, a sharp signal band may not be obtained when the analyte is detected. Hence, there is disclosed that in order to control spreading of the biomaterial-containing solution, a control line is formed in the spreading strip using a casein solution or the like, and the biomaterial-containing solution is dropped in the vicinity of the control line to thereby localize the biomaterial along the control line (see PTL 1).

CITATION LIST

Patent Literature

PTL 1 Japanese Patent Application Laid-Open (JP-A) No. 2009-264879

SUMMARY OF INVENTION

Technical Problem

However, even when the reagent is placed locally along the control line, there is a reagent concentration difference, because the concentration of the reagent is lower at a position farther from the control line. This causes a problem of poor visibility that a color development as a signal of analyte detection appears to be bleeding.

Solution to Problem

A testing device of the present invention includes:
a flow path in which an analyte is flowed,
wherein a composition containing a reagent reactive with the analyte and a lyophilic resin is placed at one position or a plurality of positions in the flow path.

Advantageous Effects of Invention

As explained above, a composition containing a reagent reactive with an analyte and a lyophilic resin is placed in the flow path of the testing device of the present invention. This produces an effect of improving the visibility of a signal when an analyte is detected.

DESCRIPTION OF EMBODIMENTS

An embodiment of the present invention will be explained below with reference to the drawings.

<<Whole Configuration of Embodiment>>

Figure 1:
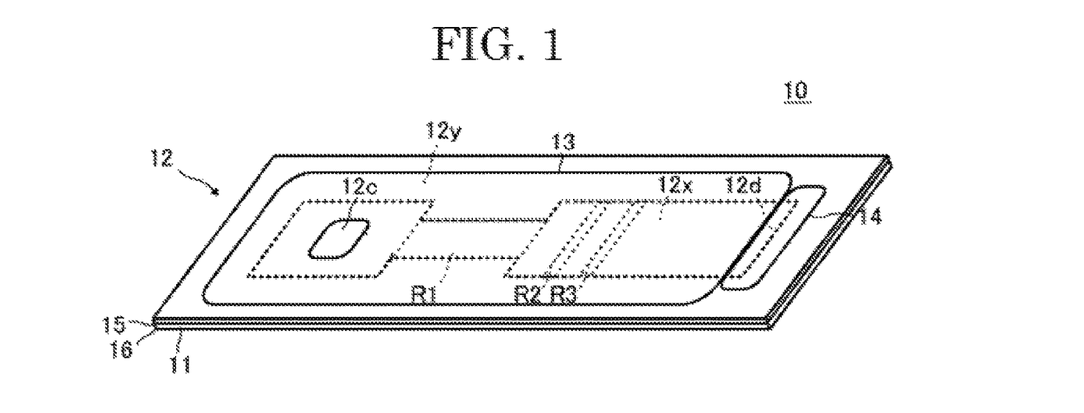
FIG. 1 is a perspective diagram of a testing device according to an embodiment of the present invention.
Figure 2:
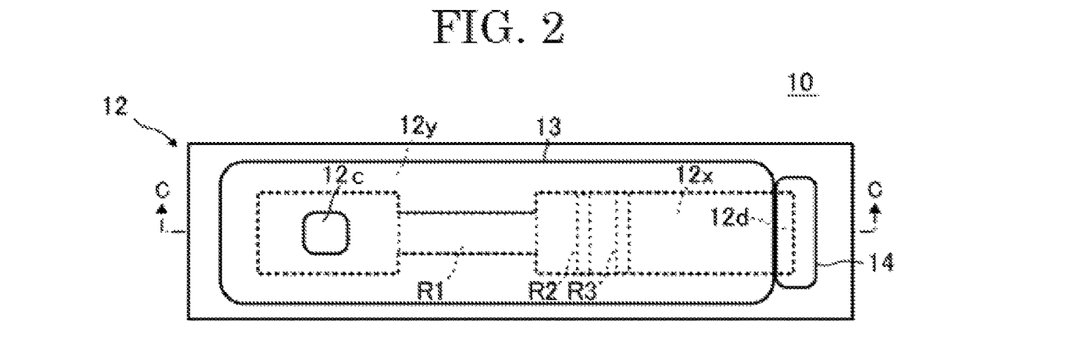
FIG. 2 is a plan view of a testing device according to an embodiment of the present invention.
Figure 3:
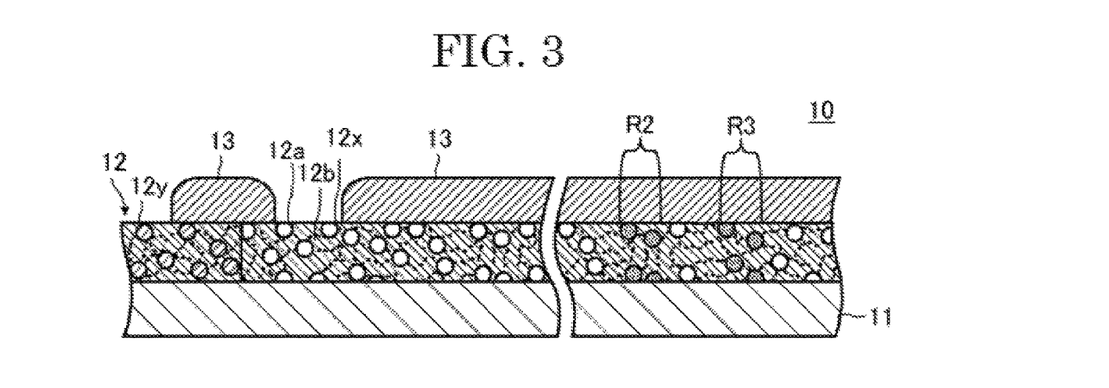
FIG. 3 is a cross-sectional diagram of a testing device according to an embodiment of the present invention.

The whole configuration of an embodiment will be explained with reference to FIG. 1 to FIG. 3. FIG. 1 is a perspective diagram of a testing device according to an embodiment of the present invention. FIG. 2 is a plan view of a testing device according to an embodiment of the present invention. FIG. 3 is a cross-sectional diagram of the testing device of FIG. 2 taken along a line C-C.

The testing device 10 shown in FIG. 1 to FIG. 3 includes a base member 11, a flow path member 12, a barrier member 13, and an absorbent member 14. The flow path member 12 of the testing device 10 includes flow paths (pores) through which an analyte liquid containing an analyte is flowed from a dropping region 12c to an absorbent region 12d (see FIG. 3). Reaction fields (R2 and F3) in which a reagent composition (an example of a composition) that contains a reagent reactive with the analyte and a lyophilic resin is placed are provided between the dropping region 12c (an example of one end of a flow path) of the analyte liquid and the absorbent region 12d (an example of the other end). The positions and the number of the reaction fields are not particularly limited, and reaction fields may be provided at one or a plurality of positions of the flow path. In this case, the lyophilic resin of the reagent placed in the flow path makes it less easy for the reagent to be spread, which makes it less likely for a reagent concentration difference to occur in the reaction fields (R2 and R3). This makes it less likely for a signal when an analyte is detected in R2 and R3 to bleed, resulting in good visibility.

In an embodiment of the present invention, a reagent is placed in the reaction fields (R2 and R3) by thermal transfer. In this case, if a transfer member in which the reagent is dispersed sufficiently in the lyophilic resin is used, there will occur a smaller reagent concentration difference in the reaction fields (R2 and F3). When placing the signal by coating, it is necessary to dilute the lyophilic resin with a solvent to a coatable viscosity (e.g., a level at which the resin can be discharged from an inkjet printer), which limits the coating amount. However, when placing the reagent and the lyophilic resin by thermal transfer as in the present embodiment, it is possible to dissolve or disperse the reagent in the lyophilic resin at a high concentration. Therefore, it is possible to place a reagent having a high concentration in the flow path. This will improve the detection sensitivity. Further, if a lyophilic resin having a high affinity with a fluid contained in an analyte, or with a solvent or a dispersion medium of the analyte is used, a contact area between the reagent composition and the analyte will be increased, and the detection sensitivity will be improved.

As an embodiment of the present invention, a case where the analyte liquid contains water and the lyophilic resin is a hydrophilic resin will be explained below. However, the present invention is not limited to this embodiment, and for example, the liquid may be an organic solvent, and the lyophilic resin may be lyophilic to this organic solvent. The organic solvent is not particularly limited, and examples thereof include: alcohols such as methyl alcohol, ethyl alcohol, 1-propyl alcohol, and 2-propyl alcohol; and ketones such as acetone and MEK (methyl ethyl ketone). As the lyophilic resin with respect to an organic solvent, various publicly-known materials are used depending on the kind of the organic solvent.

In an embodiment, a contact angle between a base member and water can be used as a degree of hydrophilicity or hydrophobicity. In this case, a substance having a large contact angle can be regarded as having a high hydrophobicity. In this case, a substance having a contact angle to water of 45 degrees or less at room temperature can be regarded as hydrophilic, and a substance having a contact angle to water of 60 degrees or greater at room temperature can be regarded as hydrophobic, where the contact angles are measured based on the coordinates on a water droplet image according to an ATAN1/2θ method and a close-up method based on Young's equation, which is a contact angle measurement model used the most commonly in various fields internationally as a formula for calculating a contact angle.

<<Base Member>>

In an embodiment of the present invention, the flow path member 12 may be provided over the base member 11 as shown in FIG. 1 to FIG. 3. the base member 11 is not particularly limited, and any base member that is organic, inorganic, or metallic may be used according to the purpose. Although not limiting, it is preferable that at least one side of the base member 11 be covered with a hydrophobic resin. When the testing device 10 is used as a sensor chip, it is preferable to use a synthetic resin that is lightweight, flexible, and inexpensive as the base member 11. Further in the present embodiment, a base member 11 having a high durability, such as a plastic sheet, can be selected. As a result, the durability of the testing device 10 will also be improved.

Examples of the base member 11 include base members made of polyvinyl chloride, polyethylene terephthalate, polypropylene, polystyrene, polyvinyl acetate, polycarbonate, polyacetal, modified polyphenyl ether, polybutylene terephthalate, and an ABS resin. Among these, a base member 11 made of polyethylene terephthalate is particularly preferable because it is inexpensive and versatile.

The shape of the base member 11 is not particularly limited, but a sheet shape is preferable. The average thickness of the base member 11 is not particularly limited and may be appropriately selected according to the purpose. However, it is preferably from 0.01 mm to 0.5 mm. In the present embodiment, the thickness of the measurement target may be measured with a micrometer from a total of 15 positions of the measurement target, namely 5 positions in the longer direction and 3 positions in the width direction that are defined at substantially equal intervals, and the average of the measured values may be used as the average thickness, although this is not particularly limiting. In the present embodiment, the thickness may be the length of the measurement target in the direction perpendicular to the interface at which the base member 11 and the flow path member 12 contact each other. When the average thickness is less than 0.01 mm, the base member 11 may not be able to maintain the strength enough to qualify as a base member. When the average thickness is greater than 0.5 mm, the base member may have insufficient flexibility depending on the material, and may be difficult to use as a sensor.

<<Flow Path Member>>

The flow path member 12 of the fluidic device 10 is not particularly limited, and examples thereof include a member made of a hydrophilic porous material that is partially hydrophobized to form a pattern for defining a flow path. Such a flow path member 12 includes a porous portion 12$x$ that is not hydrophobized, and a flow path wall 12$y$ that is hydrophobized, as shown in FIG. 3. The porous portion 12$x$ includes pores (12$a$ and 12$b$). A flow path is formed when a liquid flows through the pores (12$a$ and 12$b$). In FIG. 3, a void 12$a$ is a void formed in a cross-section of FIG. 2 taken along a line C-C. A void 12$b$ is a void in a deeper portion of the cross-section. It is preferable that cells be present in the hydrophilic porous material, and that the cells be linked and form a continuous cell. A continuous cell is different from independent cells that are not linked. The cells forming a continuous cell have a minute pore in the wall between the cells. Therefore, the continuous cell has a function of absorbing a liquid by means of a capillary action or letting a gas pass through. The flow path member 12 delivers a liquid by utilizing a capillary action. Therefore, an external actuator such as a pump is unnecessary.

The hydrophilic porous material is not particularly limited, and an appropriate one may be selected according to the purpose. However, it is preferably a base member having hydrophilicity and a high voidage. A hydrophilic porous material is a porous material into which an aqueous solution can easily penetrate. A material can be said to be easily penetrable, when in a test for water penetrability evaluation, a plate-shaped test piece of the material is dried for 1 hour at 120° C., pure water (0.01 mL) is dropped down onto the surface of the dried test piece, and the pure water (0.01 mL) completely penetrates into the test piece within 10 minutes.

The voidage of the hydrophilic porous material is not particularly limited, and may be appropriately selected according to the purpose. However, it is preferably from 40% to 90%, and more preferably from 65% to 80%. When the voidage is greater than 90%, the hydrophilic porous material may not be able to keep the strength to qualify as a base member. When the voidage is less than 40%, the penetrability of an analyte liquid may be poor.

The voidage can be calculated according to the calculation formula 1 below, based on the basis weight (g/m$^2$) and the thickness (μm) of the hydrophilic porous material, and the specific gravity of the component thereof.

Voidage (%)={1−[basis weight (g/m$^2$)/thickness (μm)/specific gravity of the component]}×100   [Calculation Formula 1]

The hydrophilic porous material is not particularly limited, and an appropriate one may be selected according to the purpose. Examples thereof include filter paper, regular paper, high-quality paper, watercolor paper, Kent paper, synthetic paper, synthetic resin film, special-purpose paper having a coating, fabric, fiber product, film, inorganic substrate, and glass.

Examples of the fabric include artificial fiber such as rayon, bemberg, acetate, nylon, polyester, and vinylon, natural fiber such as cotton and silk, blended fabric of those above, or non-woven fabric of those above.

Among these, filter paper is preferable because it has a high voidage and a favorable hydrophilicity. When the testing device 10 is used as a biosensor, filter paper is preferable as the stationary phase of paper chromatography.

The shape and average thickness of the hydrophilic porous material are not particularly limited and may be appropriately selected according to the purpose. However, a preferable shape of the hydrophilic porous material is a sheet-shape. The average thickness of the hydrophilic porous material is not particularly limited and may be appropriately selected according to the purpose. However, it is preferably from 0.01 mm to 0.3 mm. When the average thickness is less than 0.01 mm, the hydrophilic porous material may not be able to keep the strength to qualify as a base member. When the average thickness is greater than 0.3 mm, it may be less easy to form a barrier portion described later in the hydrophilic porous material.

The flow path wall 12y has hydrophobicity. Hydrophobicity means that the flow path wall is not eroded or destroyed by an aqueous fluid (e.g., an analyte liquid) moving through the flow path of the flow path member 12, or has a barrier property against water. A hydrophobizing method is not particularly limited. Examples thereof include a method of filling the voids of the hydrophilic porous material with, for example, a thermoplastic material, and according to necessity, further with other flow path wall forming materials such as an organic fatty acid, a long-chain alcohol, and other components appropriately selected.

It is possible to hydrophobize the hydrophilic porous material by transferring the flow path wall forming materials into the hydrophilic porous material, as will be described later. In the following explanation for each of the flow path wall forming materials such as a thermoplastic material, characteristics related with this method will also be explained, where appropriate.

<Thermoplastic Material>

A thermoplastic material for flow path wall formation is not particularly limited, and an appropriate one may be selected according to the purpose, as long as it has durability with which the structure of the testing device 10 is not easily collapsed when it is impregnated with water. For example, the thermoplastic material is preferably at least one selected from fat and oil, and thermoplastic resin.

—Fat and Oil—

The fat and oil means fat, fatty oil, and brazing material that are solid at normal temperature.

The fat and oil is not particularly limited, and an appropriate one may be selected according to the purpose. Examples thereof include carnauba wax, paraffin wax, microcrystalline wax, paraffin oxide wax, candelilla wax, montan wax, ceresin wax, polyethylene wax, polyethylene oxide wax, castor wax, beef tallow hardened oil, lanolin, Japan tallow, sorbitan stearate, sorbitan palmitate, stearyl alcohol, polyamide wax, oleylamide, stearylamide, hydroxystearic acid, synthetic ester wax, synthetic alloy wax, and sunflower wax. One of these may be used alone, or two or more of these may be used in combination. Among these, candelilla wax and synthetic ester wax are preferable because they can easily realize formation of the flow path wall 12y.

—Thermoplastic Resin—

The thermoplastic resin is not particularly limited, and an appropriate one may be selected according to the purpose. Examples thereof include polyolefin such as polyethylene and polypropylene, and a polyamide-based resin such as polyethylene glycol, polyethylene oxide, an acrylic resin, a polyester resin, an ethylene/vinyl acetate copolymer, an ethylene/acrylate copolymer, a urethane resin, cellulose, a vinyl chloride/vinyl acetate copolymer, a petroleum resin, a rosin resin, nylon, and copolymer nylon. One of these may be used alone or two or more of these may be used in combination.

Each thermoplastic material may be used as it is, but it is preferable that it be contained in the form of an emulsion together with an organic fatty acid and a long-chain alcohol. In this case, when the thermoplastic material is heated by a thermal head, separation preferentially occurs at the boundary between the particles having formed the emulsion, to break away the particles and transfer them into the surface of the hydrophilic porous base member. Therefore, the edge portions of the transferred material become sharp. Further, because the thermoplastic material emulsion is aqueous, it is advantageous in terms of having low environmental impact.

The method for forming an aqueous emulsion of the thermoplastic material is not particularly limited, and an appropriate method may be selected according to the purpose. Examples include a method of emulsifying the thermoplastic material by adding an organic fatty acid and an organic base to water and using the produced salt as an emulsifying agent.

The melting start temperature of the thermoplastic material is not particularly limited and may be appropriately selected according to the purpose. However, it is preferably from 50° C. to 150° C., and more preferably from 60° C. to 100° C. When the melting start temperature is lower than 50° C., storage stability under high-temperature conditions may be poor. When it is higher than 150° C., transferability during thermal transfer may be poor.

The melting start temperature of the thermoplastic material means a flowing start temperature that is observed by hardening the thermoplastic material, introducing it into a cylinder-shaped vessel having an opening with a diameter of 0.5 mm in the bottom, setting the vessel on an elevated flow tester (product name: SHIMADZU FLOW TESTER CFT-100D manufactured by Shimadzu Corporation), raising the temperature of the sample at a constant rate of 5° C./min under a load of a cylinder pressure of 980.7 kPa, and measuring the melt viscosity and flow properties of the sample along with the temperature rise.

The content of the thermoplastic material in the flow path wall forming materials is not particularly limited and may be appropriately selected according to the purpose. However, it is preferably 75% by mass or greater. When the content is less than 75% by mass, the sensitivity to heat as a transfer member may be poor.

<Organic Fatty Acid>

The organic fatty acid for flow path wall formation is not particularly limited, and an appropriate one may be selected according to the purpose. However, an organic fatty acid that has a predetermined acid value and a predetermined melting point is preferably used. The acid value of the organic fatty acid is not particularly limited and may be appropriately selected according to the purpose. However, it is preferably from 90 mgKOH/g to 200 mgKOH/g, and more preferably from 140 mgKOH/g to 200 mgKOH/g. When the acid value is less than 90 mgKOH/g, the organic fatty acid may not be able to make an emulsion of the thermoplastic material. When the acid value is greater than 200 mgKOH/g, the organic fatty acid is able to make an emulsion, but may make the emulsion creamy. Therefore, the thermoplastic material may not be prepared as a coating liquid in the production of the transfer member.

The organic fatty acid having an acid value in the range described above is not particularly limited, and an appropriate one may be selected according to the purpose. Examples thereof include an oleic acid (with an acid value of 200 mgKOH/g), a behenic acid (with an acid value of 160 mgKOH/g), and a montanic acid (with an acid value of 132 mgKOH/g).

The acid value can be measured by, for example, dissolving the sample in a mixture solvent of toluene, isopropyl alcohol, and a small amount of water, and titrating the sample with a potassium hydroxide solution.

The melting point of the organic fatty acid is not particularly limited and may be appropriately selected according to the purpose. However, it is preferably from 70° C. to 90° C. When the melting point is within the preferable value range, it is close to the melting start temperature of the thermoplastic material, which makes the sensitivity property favorable. When the melting point is lower than 70° C., the flow path wall $12y$ may be softened under high-temperature conditions such as summertime.

The organic fatty acid having a melting point in the range described above is not particularly limited, and an appropriate one may be selected according to the purpose. Examples thereof include a behenic acid (with a melting point of 76° C.) and a montanic acid (with a melting point of 80° C.).

The melting point can be measured by using a differential scanning calorimeter "DSC7020" (manufactured by Seiko Instruments, Inc.) and measuring the temperature at which a crystal melting endothermic peak that is to appear in a temperature raising measurement with the differential scanning calorimeter ends.

The content of the organic fatty acid is not particularly limited and may be appropriately selected according to the purpose. However, it is preferably from 1 part by mass to 6 parts by mass relative to 100 parts by mass of the thermoplastic material. When the content is less than 1 part by mass, the organic fatty acid may not be able to make the thermoplastic material an emulsion, when preparing a coating liquid used for production of the transfer member. When the content is greater than 6 parts by mass, blooming of the thermoplastic material may occur.

<Long-Chain Alcohol>

The long-chain alcohol is not particularly limited, and an appropriate one may be selected according to the purpose. However, at least any selected from a long-chain alcohol represented by General Formula (1) below and a long-chain alcohol represented by General Formula (2) below is preferable.

General Formula (1)

In General Formula (1), $R^1$ represents an alkyl group having 28 to 38 carbon atoms.

General Formula (2)

In General Formula (2), $R^2$ represents an alkyl group having 28 to 38 carbon atoms.

The long-chain alcohol is not particularly limited, and an appropriate one may be selected according to the purpose. However, it is preferably an aliphatic alcohol having a melting point of from 70° C. to 90° C. When the melting point is lower than 70° C., the flow path wall $12y$ may be softened under high-temperature conditions such as summertime. When the melting point is higher than 90° C., the transferability may be poor. When the melting point is within the preferable value range, it is close to the melting start temperature of the thermoplastic material, which makes the transferability of the transfer member favorable. The melting point can be measured by the same method for measuring the melting point of the organic fatty acid.

The long chain of the long-chain alcohol may be composed only of a straight chain, or may have branched chains. The number of carbon atoms on the long chain (the number of carbon atoms in the alkyl group) is not particularly limited and may be appropriately selected according to the purpose. However, it is preferably from 28 to 38. When the number of carbon atoms is not within the above value range, the transfer member may cause blooming along with the elapse of time, and may contaminate the surroundings when it is stored in a rolled shape.

The content of the long-chain alcohol is not particularly limited and may be appropriately selected according to the purpose. However, it is preferably from 6 parts by mass to 12 parts by mass relative to 100 parts by mass of the thermoplastic material. When the content is less than 6 parts by mass, the blooming suppression effect may not be obtained. When the content is greater than 12 parts by mass, the transferability of the transfer member may be poor when the long-chain alcohol has a temperature difference from the melting start temperature of the thermoplastic material.

<Other Components>

The other components are not particularly limited, and appropriate ones may be selected according to the purpose. Examples thereof include an organic base, a non-ionic surfactant, and a colorant.

—Organic Base—

The organic base may be used together with the organic fatty acid when emulsifying the thermoplastic material.

The organic base is not particularly limited, and an appropriate one may be selected according to the purpose. However, morpholine is preferable because it easily volatilizes after dried. The content of the organic base is not particularly limited and may be appropriately selected according to the purpose. However, it is preferably from 0.5 parts by mass to 5 parts by mass relative to 100 parts by mass of the thermoplastic material.

—Non-Ionic Surfactant—

Addition of the non-ionic surfactant enables the particle diameter of the aqueous emulsion of the thermoplastic material to be small, which improves the cohesive force of the flow path wall $12y$ and enables prevention of a background smear. The non-ionic surfactant is not particularly limited, and an appropriate one may be selected according to the purpose. Examples thereof include POE oleylether.

The content of the non-ionic surfactant is not particularly limited and may be appropriately selected according to the purpose. However, it is preferably from 2 parts by mass to 7 parts by mass relative to 100 parts by mass of the thermoplastic material. When the content is less than 2 parts by mass, the effect of making the particle diameter of the aqueous emulsion of the thermoplastic material small may be poor when making an aqueous emulsion of the thermoplastic material. When the content is greater than 7 parts by mass, the flow path wall $12y$ forming layer may become soft to degrade the friction resistance of the flow path wall $12y$.

—Colorant—

The colorant may be added in order to impart the function for enabling the flow path wall $12y$ to be distinguished in the flow path member 12. The colorant is not particularly limited, and an appropriate one may be selected according to the purpose. Examples thereof include carbon black, an azo-based pigment, phthalocyanine, quinacridone, anthraquinone, perylene, quinophthalone, aniline black, titanium oxide, zinc oxide, and chromium oxide. Among these, carbon black is preferable.

The content of the colorant is not particularly limited and may be appropriately selected according to the purpose. However, it is preferably from 0.5 parts by mass to 5 parts by mass relative to 100 parts by mass of the thermoplastic material.

The shape of the flow path wall $12y$ is not particularly limited and may be appropriately selected according to the purpose. Examples thereof include one of a straight line, a curve, and a junction of a plurality of branches, or combinations of these.

The pattern width of the flow path wall $12y$ (the width of a wall portion) is not particularly limited, and patterning may be applied with an arbitrary width according to the size of the testing device 10. However, the width is preferably 500 µm or greater. When the pattern width is less than 500 µm, the voids in the hydrophilic porous base member may be insufficiently filled with the hydrophobizing materials, which may make the flow path wall unable to function as a liquid-impenetrable barrier.

According to an embodiment of the present invention, the flow path wall $12y$ may be formed to have an arbitrary length in the direction of thickness of the hydrophilic porous material from the surface thereof into the interior thereof, i.e., in the direction of depth. Factors that control the length include the melt viscosity and the hydrophilicity of the fat and oil or the thermoplastic resin. The lower the melt viscosity, the easier it becomes for the fat and oil or the thermoplastic resin to penetrate into the interior of the hydrophilic porous material from the surface thereof, which enables a long length. Conversely, the higher the melt viscosity, the harder it becomes for the fat and oil or the thermoplastic resin to penetrate into the interior of the hydrophilic porous material from the surface thereof, which enables a substantially non-penetrated state. It is possible to control the thickness by controlling the melt viscosity.

Meanwhile, as for the hydrophilicity of the fat and oil and the thermoplastic resin, ones with a higher hydrophilicity can more easily penetrate into the interior of the hydrophilic porous material from the surface thereof, which enables a long length. Conversely, ones with a lower hydrophilicity can more hardly penetrate into the interior of the hydrophilic porous material from the surface thereof, which enables a substantially non-penetrated state. It is possible to control the thickness by controlling the hydrophilicity, but the melt viscosity influences the penetrability much more than the hydrophilicity does.

The melt viscosity of the thermoplastic material varies depending also on the hydrophilicity of the hydrophilic porous material, or the fat and oil or the thermoplastic resin. Therefore, the value range of the melt viscosity to be mentioned below does not necessarily apply, but the thermoplastic material (the fat and oil, and the thermoplastic resin), if it is used in a hydrophilic porous base member such as cellulose, can be freely and arbitrarily selected from materials of a very broad viscosity range of from 3 mPa·s to 1,600 mPa·s, and can be thermally transferred. In particular, in order to make the flow path wall forming materials penetrate into the interior of the hydrophilic porous material from the surface thereof so as to make the length of the flow path wall in the direction of thickness large, it is preferable to use a thermoplastic material having a melt viscosity of from 6 mPa·s to 200 mPa·s. Meanwhile, conventional techniques include an inkjet system.

For example, an inkjet printer using an ultraviolet curable resin ink discharges the ink from the head and makes the ink droplets fly and land into a porous layer. Therefore, there is a limitation; in order for a liquid to be discharged from the head, the viscosity of the liquid needs to be as low as 15 mPa·s at the maximum, or needs actually to be lower than 10 mPa·s, or otherwise the liquid cannot be discharged from the head, which allows poor latitude in the selection of the material. For this reason, the ink that can be used in the inkjet printer has a very low viscosity, and hence easily spreads in a porous layer, making a large bleed.

The same can be said for a wax printer. A wax printer thermally melts a solid ink and discharges the ink from the head to make droplets of the melted ink fly and land into a porous layer. Therefore, there is the same viscosity limitation as described above, in order for the ink to be discharged from the head, resulting in a poor latitude in the selection of the material. Besides, in the case of a wax printer, in reality, the temperature of the solid ink lowers during the flight to thereby make the viscosity have already risen above the level at which the ink can penetrate into the porous layer when the ink droplets land on the porous layer. Therefore, the ink droplets stop on the surface of the porous layer and cannot penetrate into the interior of the porous layer. This indispensably necessitates a step of heating the porous layer to a temperature at which the thermoplastic material can melt sufficiently in order to make the material penetrate. Therefore, not only does the process become complicated, but the porous layer cannot avoid being entirely heated, which makes it easier for the ink to spread also in the horizontal direction, making a large bleed.

In contrast, the thermal transfer system performs printing by bringing the thermal head into direct contact with a porous layer via the flow path wall forming transfer member. Therefore, the thermal head applies heat only locally to a minute portion to which to transfer the ink, which enables effective suppression of the spreading of the thermoplastic material in the horizontal direction, resulting in a highly linear flow path with no bleed.

The length can also be controlled by controlling the energy to be applied for thermal compression bonding. That is, the more the energy to be applied is increased to raise the temperature of the fat and oil, and the thermoplastic resin, which are the thermoplastic material, the more inward they penetrate, whereas the more the temperature is lowered, the closer to the surface they stop.

<<Reaction Field>>

Reaction fields (R1, R2, and R3) are provided in the porous portion $12x$ of the flow path member 12 for reactions of an analyte liquid and a reagent. In the testing device 10 shown in FIG. 1 to FIG. 3, the reaction field R1 is a region in which to elute the antibody applied in the reaction field R1 from the porous base member, to let it undergo an antigen-antibody reaction with an antigen in the analyte liquid. The reaction field R2 is a region in which to provide a test line for trapping an antigen-labeled antibody linkage formed in the reaction field R1 and showing a color reaction. The reaction field R3 is a control line for trapping a labeled antibody and showing a color reaction, which is provided for the purpose of confirming whether the analyte liquid has reached the reaction field R3 infallibly.

The reagent placed in the reaction field R1 is not particularly limited, and examples thereof include a gold colloid-labeled antibody such as gold colloid-labeled anti-human IgG.

The reagent placed in the reaction field R2 is not particularly limited, and examples thereof include anti-human IgG.

The reagent placed in the reaction field R3 is not particularly limited, and examples thereof include human IgG.

Figure 7:
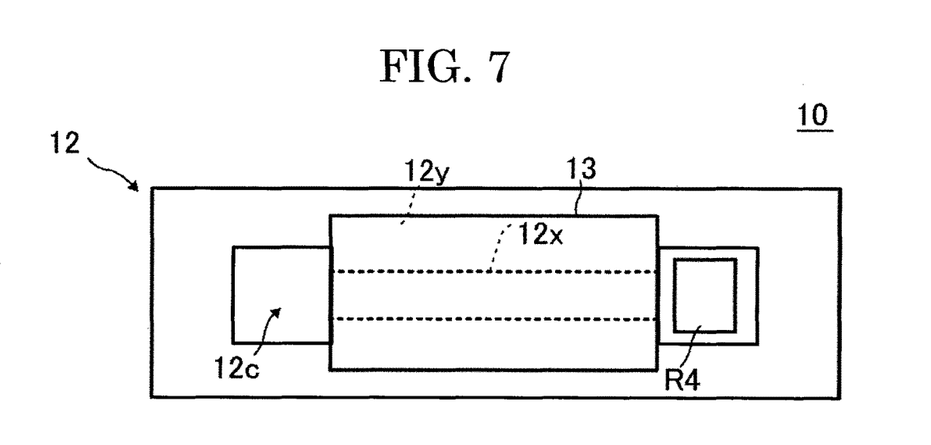
FIG. 7 is a plan view of a testing device.

A reaction field of a testing device 10 having a different shape will be explained with reference to FIG. 7. FIG. 7 is a plan view of a testing device. In FIG. 7, a reaction field R4 is provided in the porous portion 12x of the flow path member 12, for reactions between an analyte liquid and a reagent. The reaction field R4 is provided for performing colorimetric detection in response to a change in the hue, which is due to a change in the chemical structure, or a physical structural change (e.g. an agglomerated state) of the pigment, etc.

The reagent placed in the reaction field R4 is not particularly limited, and examples thereof include a pH indicator, various ionophores that change colors by reacting with various ions such as a lead ion, a copper ion, and a nitrite ion, and a reagent that changes colors by reacting with various agricultural chemicals.

At least one or preferably all of the reaction fields (R1, R2, R3, and R4) are provided by placing a reagent composition containing the reagent described above and a hydrophilic resin in the pores (flow paths) of the porous portion 12x. A hydrophilic resin is a resin of which contact angle is 45 degrees or less, where the contact angle is measured based on the coordinates on a water droplet image according to an ATAN1/2θ method and a close-up method based on Young's equation, which is a contact angle measurement model used the most commonly in various fields internationally as a formula for calculating a contact angle. With the use of a hydrophilic resin having a high affinity with a liquid contained in an analyte, or with water as a solvent or a dispersion medium of the analyte, the contact area between the reagent composition and the analyte will be large, and the detection sensitivity will be improved. The hydrophilic resin is not particularly limited, and examples thereof include poly(ethylene oxide), polyvinyl alcohol, polyvinyl pyrrolidone, polyacrylic acid, polyhydroxyethyl, polyacrylamide, polyethylene glycol, polyethylene oxide, polyamide, polyvinyl sulfonic acid, polystyrene sulfonic acid, polyacrylamide sulfonic acid, and a butyral resin.

Among these, poly(ethylene oxide), polyvinyl pyrrolidone, and polyacrylic acid are preferable because they are excellent in a film forming property and adhesiveness. Specific examples of poly(ethylene oxide) include ALKOX® SERIES manufactured by Meisei Chemical Works, Ltd.

In terms of thermal transferability, it is preferable that the hydrophilic resin be a thermoplastic material. In this case, the melt viscosity of the hydrophilic resin at 120° C. is preferably from 3 mPa·s to 1,600 mPa·s, and more preferably from 6 mPa·s to 200 mPa·s. When the melt viscosity is less than 3 mPa·s, the hydrophilic resin may be, when thermally transferred, spread in the hydrophilic porous base member also in the horizontal direction thereof, to thereby cause difference in the reagent composition concentration. When the melt viscosity is greater than 1,600 mPa·s, the hydrophilic resin may persist on the support member of the reagent composition transfer member, and a necessary amount of the hydrophilic resin may not be fully thermally transferred. Further, it is preferable that the hydrophilic resin be a water-soluble resin, in terms of performing chromatography without inhibiting the flow of the analyte liquid.

It is preferable that the reagent composition be fixed in the pores (flow paths) of the porous portion 12x, in order to prevent the reagent from being spread. The state of the reagent composition being fixed means that, for example, the reagent composition is filled in the pores of the porous portion 12x along the pores and cannot move relative to the porous portion 12x. The method for fixing the reagent composition in the pores is not particularly limited, and examples thereof include a method of solidifying a melted reagent composition in the pores.

The method for producing a composition containing a reagent and a hydrophilic resin is not particularly limited, and examples thereof include a method of dissolving a reagent and a hydrophilic resin in a solvent, mixing the reagent and the hydrophilic resin until they are dispersed uniformly, and then desolventize the resultant by drying.

<<Absorbent Member>>

The absorbent member 14 is not particularly limited except that it should be able to absorb water, and such an absorbent member may be selected from publicly-known materials. Examples of such an absorbent member 14 includes paper, fiber such as fabric, a polymeric compound having a carboxyl group or a salt thereof, a partially cross-linked product of a polymeric compound having a carboxyl group or a salt thereof, and a partially cross-linked product of a polysaccharide.

<<Barrier Member>>

In the present embodiment, the barrier member 13 contacts the flow path wall 12y of the flow path member 12 and the absorbent member 14, and covers at least a portion of the absorbent member 14. The barrier member 13 has a barrier property against water, and preferably has a gas barrier property. Having a gas barrier property means that the barrier member has a smaller gas permeability than that of at least paper. Preferable examples of the constituent material of the barrier member 13 include materials such as a film and a laminate that have a water gas permeability (water vapor permeability) of 100 g/(m²·day) or less, preferably 50 g/(m²·day) or less, and more preferably 10 g/(m²·day) or less, where the water gas permeability is measured according to ISO15106-1. Examples of materials having a water gas permeability of 50 g/(m²·day) include a polyethylene wax, a polypropylene wax, a silicone resin, polycarbonate, and polystyrene. The thickness of the barrier member 13 is not particularly limited, but is preferably from 5 μm to 100 μm, and more preferably from 10 μm to 70 μm. When the thickness is less than 5 μm, the barrier member may not be able to have a sufficient gas shielding property to thereby promote drying over time. When the thickness is greater than 100 μm, the barrier member may have a poor adhesiveness with respect to the flow path member.

Use of the barrier member 13 in this way prevents a hand from being contaminated when touching the testing device 10. Therefore, the testing device needs no housing.

A material preferable as the material of the barrier member 13 is not particularly limited, and examples thereof include waxes such a candelilla wax, polyamides such as nylon, and resins such as an ethylene/vinyl alcohol copolymer resin (EVOH) and a polyvinylidene chloride resin. These materials have thermoplasticity, and are preferable in thermal transferability, a film forming property, or the like. The same thermoplastic materials as the flow path wall forming materials to be described later may be used as these materials. Among these, the waxes such as a candelilla wax are preferable in terms of releasability during thermal transfer. Note that resins are preferable when a gas barrier property is required.

<<Transfer Member for Flow Path Wall Formation>>

Figure 4:
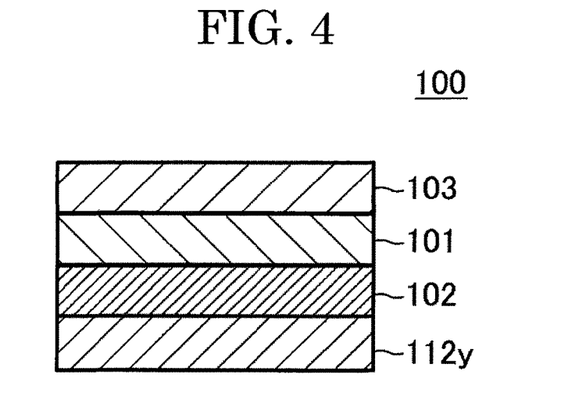
FIG. 4 is a cross-sectional diagram of a transfer member for flow path wall formation according to an embodiment of the present invention.

Next, a method for forming the flow path member 12 by transferring the flow path wall forming material into the hydrophilic porous material will be explained. First, the transfer member for flow path wall formation will be explained with reference to FIG. 4. FIG. 4 is a cross-sectional diagram of the transfer member for flow path wall formation. The transfer member for flow path wall formation 100 is obtained by stacking a releasing layer 102 and a flow path wall forming layer 112y in this order over a support member 101, and includes other layers according to necessity.

<Support Member>

The shape, structure, size, material, etc. of the support member 101 are not particularly limited, and may be appropriately selected according to the purpose. The structure may be a single-layer structure, or may be a layered structure. The size of the support member may be appropriately selected according to the size of the testing device 10, etc.

The material of the support member 101 is not particularly limited, and may be appropriately selected according to the purpose. Examples thereof include polyester such as polyethylene terephthalate (PET) and polyethylene naphthalene (PEN), polycarbonate, a polyimide resin (PI), polyamide, polyethylene, polypropylene, polyvinyl chloride, polyvinylidene chloride, polystyrene, a styrene/acrylonitrile copolymer, and cellulose acetate One of these may be used alone, or two or more of these may be used in combination. Among these, polyethylene terephthalate (PET) and polyethylene naphthalate (PEN) are particularly preferable.

It is preferable to perform a surface activation treatment on the surface of the support member 101, in order to improve close adhesiveness with respect to the layer to be provided over the support member 101. Examples of the surface activation treatment include a glow discharge treatment, and a corona discharge treatment.

The support member 101 may be kept after having transferred the flow path wall forming layer 112y into the hydrophilic porous material. Alternatively, the support member 101 may be peeled and removed by means of the releasing layer 102, after having transferred the flow path wall forming layer 112y. The support member 101 is not particularly limited, and may be an appropriately synthesized product or may be a commercially available product. The average thickness of the support member 101 is not particularly limited, and may be appropriately selected according to the purpose. However, it is preferably from 3 µm to 50 µm.

<Releasing Layer>

The releasing layer 102 has a function of improving separability between the support member 101 and the flow path wall forming layer 112y during transfer. The releasing layer 102 also has a function of thermally melting to a low viscosity liquid when heated with a heating/pressurizing unit such as a thermal head to thereby make it easier for the flow path wall forming layer 112y to be separated at the interface between the heated portion and a non-heated portion. The releasing layer 102 contains a wax and a binder resin, and further contains other components appropriately selected according to necessity.

—Wax—

The wax is not particularly limited, and an appropriate one may be selected according to the purpose. Examples thereof include: natural wax such as beeswax, carnauba wax, spermaceti, Japan tallow, candelilla wax, rice wax, and montan wax; synthetic wax such as paraffin wax, microcrystalline wax, oxide wax, ozokerite, ceresin, ester wax, polyethylene wax, and polyethylene oxide wax; higher fatty acid such as margaric acid, lauric acid, myristic acid, palmitic acid, stearic acid, furoic acid, and behenic acid; higher alcohol such as stearin alcohol and behenyl alcohol; esters such as sorbitan fatty acid ester; and amides such as stearamide and oleic amide. One of these may be used alone or two or more of these may be used in combination. Among these, carnauba wax and polyethylene wax are preferable because they are excellent in releasability.

—Binder Resin—

The binder resin is not particularly limited, and appropriate one may be selected according to the purpose. Examples thereof include an ethylene/vinyl acetate copolymer, a partially saponified ethylene/vinyl acetate copolymer, an ethylene/vinyl alcohol copolymer, an ethylene/sodium methacrylate copolymer, polyamide, polyester, polyurethane, polyvinyl alcohol, methyl cellulose, carboxymethyl cellulose, starch, polyacrylic acid, an isobutylene/maleic acid copolymer, a styrene/maleic acid copolymer, polyacrylamide, polyvinyl acetal, polyvinyl chloride, polyvinylidene chloride, an isoprene rubber, a styrene/butadiene copolymer, an ethylene/propylene copolymer, a butyl rubber, and an acrylonitrile/butadiene copolymer. One of these may be used alone, or two or more of these may be used in combination.

The method for forming the releasing layer 102 is not particularly limited, and an appropriate method may be selected according to the purpose. Examples thereof include a hot-melt coating method, and a coating method using a coating liquid obtained by dispersing the wax and the binder resin in a solvent. The average thickness of the releasing layer 102 is not particularly limited and may be appropriately selected according to the purpose. However, it is preferably from 0.5 µm to 2.0 µm. The amount of deposition of the releasing layer 102 is not particularly limited and may be appropriately selected according to the purpose. However, it is preferably from 0.5 $g/m^2$ to 8 $g/m^2$, and more preferably from 1 $g/m^2$ to 5 $g/m^2$.

<Flow Path Wall Forming Layer>

The materials, etc. of the flow path wall forming layer 112y are as described above as for the flow path wall forming materials. The method for forming the flow path wall forming layer 112y is not particularly limited, and an appropriate method may be selected according to the purpose. For example, as a hot-melt coating method or a coating method using a coating liquid obtained by dispersing the thermoplastic material in a solvent, a common coating method using a gravure coater, a wire bar coater, a roll coater, or the like may be used. According to such a method, the support member 101 or the releasing layer 102 may be coated with the flow path wall forming layer coating liquid. When they are dried, the flow path wall forming layer is formed.

The average thickness of the flow path wall forming layer 112y is not particularly limited and may be appropriately selected according to the purpose. However, it is preferably from 5 μm to 250 μm. When the average thickness is less than 5 μm, the amount of the flow path wall forming layer 112y may be insufficient for filling the voids in the hydrophilic porous material. When the average thickness is greater than 250 μm, it becomes harder for heat from the thermal head to be conducted through the flow path wall forming layer 112y, to thereby degrade the transferability.

The amount of deposition of the flow path wall forming layer 112y is not particularly limited and may be appropriately selected according to the purpose. However, it is preferably from 5 g/m$^2$ to 250.0 g/m$^2$, and more preferably from 30 g/m$^2$ to 150.0 g/m$^2$.

<Other Layers and Members>

The other layers and members are not particularly limited, and appropriate ones may be selected according to the purpose. Examples thereof include a back layer 103, an undercoat layer, and a protection film.

—Back Layer—

It is preferable that the transfer member for flow path wall formation 100 include a back layer 103 over a side of the support member 101 opposite to the side thereof over which the flow path wall forming layer 112y is formed. Heat is directly applied to this opposite side by a thermal head or the like at a position corresponding to the shape of the flow path wall. Therefore, it is preferable that the back layer 103 have resistance to high heat and resistance to friction with a thermal head or the like. The back layer 103 contains a binder resin, and further contains other components according to necessity.

The binder resin is not particularly limited, and an appropriate one may be selected according to the purpose. Examples thereof include a silicone-modified urethane resin, a silicone-modified acrylic resin, a silicone resin, a silicone rubber, a fluororesin, a polyimide resin, an epoxy resin, a phenol resin, a melamine resin, and nitrocellulose. One of these may be used alone or two or more of these may be used in combination.

The other components are not particularly limited, and appropriate ones may be selected according to the purpose. Examples thereof include inorganic particles of talc, silica, organopolysiloxane, etc., and a lubricant.

The method for forming the back layer 103 is not particularly limited, and an appropriate method may be selected according to the purpose. Examples thereof include common coating methods using a gravure coater, a wire bar coater, a roll coater, etc. The average thickness of the back layer 103 is not particularly limited and may be appropriately selected according to the purpose. However, it is preferably from 0.01 μm to 1.0 μm.

—Undercoat Layer—

An undercoat layer may be provided between the support member 101 and the flow path wall forming layer 112y, or between the releasing layer 102 and the flow path wall forming layer 112y. The undercoat layer contains a resin, and further contains other components according to necessity. The resin is not particularly limited, and an appropriate one may be selected according to the purpose. The resin may be any of the resins usable for the flow path wall forming layer 112y and the releasing layer 102.

—Protection Film—

It is preferable to provide a protection film over the flow path wall forming layer 112y for protecting the layer from contamination or damages during storage. The material of the protection film is not particularly limited, and an appropriate one may be selected according to the purpose, as long as it can be easily separated from the flow path wall forming layer 112y. Examples thereof include silicone sheet, polyolefin sheet such as polypropylene sheet, and polytetrafluoroethylene sheet. The average thickness of the protection film is not particularly limited and may be appropriately selected according to the purpose. However, it is preferably from 5 μm to 100 μm, and more preferably from 10 μm to 30 μm.

<Transfer of Flow Path Wall Forming Layer>

In the formation of the flow path wall 12y, the hydrophilic porous material and the flow path wall forming layer 112y of the transfer member for flow path wall formation 100 are faced and overlapped with each other, and the flow path wall forming layer is thermally transferred. The method for thermally transferring the flow path wall forming layer 112y is not particularly limited, and an appropriate method may be selected according to the purpose. Examples thereof include a method of melting and transferring the flow path wall forming layer 112y by thermal compression bonding with a serial thermal head, a line thermal head, etc. The energy applied in the thermal compression bonding is not particularly limited, and may be appropriately selected according to the purpose. However, it is preferably from 0.1 mJ/dot to 1.00 mJ/dot.

When the energy is lower than 0.1 mJ/dot, the flow path wall forming layer 112y may be melted insufficiently. When the energy is higher than 1.00 mJ/dot, portions of the transfer member for flow path wall formation 100 other than the flow path wall forming layer 112y may be melted and contaminate the thermal head.

<<Transfer Member for Reagent Composition Formation>>

Figure 5:
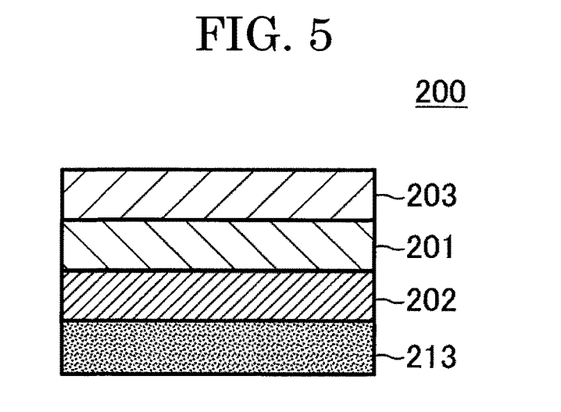
FIG. 5 is a cross-sectional diagram of a transfer member according to an embodiment of the present invention.

Next, a method for placing a reagent composition over at least one of the reaction fields (R1, R2, and R3) by transferring the reaction composition to the flow path member 12 in which the flow path wall 12y has been formed will be explained. First, a reagent composition transfer member will be explained with reference to FIG. 5. FIG. 5 is a cross-sectional diagram of a transfer member for reagent composition formation according to an embodiment of the present invention. The transfer member for reagent composition formation 200 is a transfer member for fabrication of the testing device 10, and includes a support member 201, a releasing layer 202 stacked over the support member 201, and a reagent composition forming layer 213 containing the reagent composition. The reagent composition forming layer 213 contains a thermoplastic material. The transfer member for reagent composition formation 200 further includes other layers such as a back layer 203 according to necessity.

<Support Member/Releasing Layer/Other Layers and Members>

As the support member 201, the same one as the support member 101 of the transfer member for flow path wall formation 100 is used. Therefore, a detailed explanation thereof will not be provided. As the releasing layer 202, the same one as the releasing layer 102 of the transfer member for flow path wall formation 100 is used. Therefore, a detailed explanation thereof will not be provided. As the back layer 203 and the other layers and members, the same ones as the back layer 103, and the other layers and members of the transfer member for flow path wall formation 100 are used. Therefore, a detailed explanation thereof will not be provided.

<Reagent Composition Forming Layer>

The reagent composition contained in the reagent composition forming layer 213 is as described above. The method for forming the reagent composition forming layer 213 is not particularly limited, and an appropriate method may be selected according to the purpose. For example, as a hot-melt coating method or a coating method using a coating liquid obtained by dispersing materials including the reagent and the hydrophilic resin in a solvent, a common coating method using a gravure coater, a wire bar coater, a roll coater, or the like may be used. According to such a method, the releasing layer 202 is coated with a reagent composition formation coating liquid. When the liquid is dried, the reagent composition forming layer is formed.

The average thickness of the reagent composition forming layer 213 is not particularly limited and may be appropriately selected according to the purpose. However, it is preferably from 1 μm to 15 μm. When the average thickness is less than 1 μm, it may not be possible to place the reagent in such an amount enough to ensure visibility. When the average thickness is greater than 15 μm, it may be harder for heat from a thermal head to be conducted through the reagent composition forming layer 213, to thereby degrade transferability.

The amount of deposition of the reagent composition forming layer 213 is not particularly limited and may be appropriately selected according to the purpose. However, it is preferably from 1 $g/m^2$ to 15.0 $g/m^2$, and more preferably from 1 $g/m^2$ to 10.0 $g/m^2$.

<Transfer of Reagent Composition Forming Layer>

In the formation of the reagent composition forming layer 213, the reagent composition forming layer 213 of the transfer member for reagent composition formation 200 and the flow path member 12 are faced and overlapped with each other and thereby brought into contact with each other. Then, heat and pressure are applied to the transfer member for reagent composition formation 200 to transfer the reagent composition forming layer 213 onto the flow path member 12.

The thermal transfer method is not particularly limited, and an appropriate method may be selected according to the purpose. Examples include a method of melting and transferring the reagent composition forming layer 213 by thermal compression bonding with a serial thermal head, a line thermal head, etc. The energy applied for the thermal compression bonding is not particularly limited, and may be appropriately selected according to the purpose. However, it is preferably from 0.05 mJ/dot to 0.5 mJ/dot.

When the applied energy is less than 0.05 mJ/dot, the reagent composition forming layer 213 may be melted insufficiently. When the applied energy is greater than 0.5 mJ/dot, portions of the transfer member for reagent composition formation 200 other than the reagent composition forming layer 213 may be melted and contaminate the thermal head.

<<Use Applications of Testing Device>>

The use applications of the testing device 10 are not particularly limited, and appropriate applications may be selected according to the purpose. Examples thereof include a biochemical sensor (sensing chip) for blood testing and DNA testing, and a small-size analytical device (chemical sensor) for quality control of foods and beverages.

A sample (analyte) to be used for biochemical testing is not particularly limited, and an appropriate one may be selected according to the purpose. Examples thereof include a pathogen such as a bacterium and a virus, blood, saliva, a lesional tissue, etc. separated from living organisms, and egestion such as enteruria. Further, for performing a prenatal diagnosis, the sample may be a part of a fetus cell in an amniotic fluid, or of a dividing egg cell in a test tube. Furthermore, these samples may be, after condensed to a sediment directly or by centrifugation or the like according to necessity, subjected to a pre-treatment for cell destruction through an enzymatic treatment, a thermal treatment, a surfactant treatment, and an ultrasonic treatment, or any combinations of these, etc.

The testing device of the present embodiment also has a function of performing chromatography (separation and refinement) of an analyte liquid, because the porous portion 12x serves as a stationary phase. In this case, the porous portion 12x having a continuous cell of which internal wall has hydrophilicity serves as the stationary phase (a carrier). Different compositions in the analyte liquid flow through the flow paths at different speeds because of difference in their interactions with the stationary phase during the process of their penetration through the flow paths, i.e., difference in whether they are hydrophilic or hydrophobic.

A component having a higher hydrophilicity is more likely to adsorb to the porous portion that is inward from the flow path wall and serving as the stationary phase, and repeats adsorbing and desorbing more times. Therefore, such a component penetrates through the flow paths at a lower speed. Conversely, a component having a higher hydrophobicity penetrates without adsorbing to the stationary phase. Therefore, such a component moves rapidly through the fluid paths. By utilizing the difference in the moving speed in the analyte liquid, and extracting the target component in the analyte liquid selectively and letting it undergo a reaction, it is possible to use the testing device 10 as a highly functional chemical or biochemical sensor.

<<<Testing Method>>>

A testing method using the testing device 10 is not particularly limited. Examples thereof include a method of dropping and supplying an analyte liquid containing an analyte into a dropping region 12c of the testing device 10, and making a judgment based on a reaction of the analyte flowing through the flow paths in the porous portion 12x with the reagents placed in the reaction fields (R1, R2, and R3). According to this testing method, a signal based on a reaction between the reagents and the analyte can be obtained obviously. Therefore, a judgment can be easily made.

The reaction field R1 elutes the antibody applied over the reaction field R1 from the porous base member to let it undergo an antigen-antibody reaction with the antigen in the analyte liquid. The reaction field R2 traps an antigen-labeled antibody linkage formed in the reaction field R1, and the judgment is positive when the reaction field show a color reaction upon trapping. The reaction field R3 is a control line for trapping a labeled antibody and showing a color reaction, and it shows a color reaction when the analyte liquid has reached the reaction field R3 infallibly.

EXAMPLES

Examples of the present invention will be explained below. However, the present invention is not limited to these Examples by any means. In Examples and Comparative Examples described below, the voidage of the flow path member (porous portion) was calculated as follows.

<Calculation of Voidage of Porous Portion of Flow Path Member>

The voidage of the porous portion of the flow path member was calculated according to the calculation formula 1 below based on the basis weight ($g/m^2$) and the thickness (μm) of the hydrophilic porous material, and the specific gravity of the component thereof.

Voidage (%)={1−[basis weight (g/m²)/thickness (μm)/specific gravity of the component]}×100  [Calculation Formula 1]

Example 1

<Preparation of Reagent Composition Forming Layer Coating Liquid>

Polyvinyl pyrrolidone (PVP) (5259-100GM manufactured by Merck Millipore Corporation) (15 parts by mass), a pH indicator (a 0.04% by mass bromthymol blue (BTB) solution manufactured by Wako Pure Chemical Industries, Ltd.) (60 parts by mass), purified water (manufactured by Wako Pure Chemical Industries, Ltd.) (20 parts by mass), and ethanol (manufactured by Kanto Kagaku Ptd Ltd., special grade) (15 parts by mass) were dissolved and dispersed at room temperature (25° C.), to thereby produce a reagent composition forming layer coating liquid.

<Preparation of Back Layer Coating Liquid>

An emulsion of a silicone-based rubber (KS779H manufactured by Shin-Etsu Chemical Co., Ltd., with a solid content of 30% by mass) (16.8 parts by mass), a chloroplatinic acid catalyst (0.2 parts by mass), and toluene (83 parts by mass) were mixed, to thereby obtain a back layer coating liquid.

<Preparation of Transfer Member for Reagent Composition Formation>

The back layer coating liquid was applied over one side of a polyester film having an average thickness of 4.5 μm (LUMIRROR F57 manufactured by Toray Industries, Inc.) as a support member, and dried at 80° C. for 10 seconds, to thereby form a back layer having an average thickness of 0.02 μm.

Next, the reagent composition forming layer coating liquid was applied over a side of the polyester film opposite to the side thereof over which the back layer was formed, and dried at room temperature for 60 minutes, to thereby form a reagent composition forming layer having an average thickness of 10 μm. In this way, a transfer member for reagent composition formation was produced.

<Preparation of Flow Path Wall Forming Layer Coating Liquid>

An ester wax (WE-11 manufactured by NOF Corporation, with a melting start temperature of 65° C.) (100 parts by mass), montanic acid (product name: LUWAX-E manufactured by BASF Corporation, with a melting point of 76° C.) (2 parts by mass), and a long-chain alcohol represented by General Formula (1) below (where $R^1$ was an alkyl group having 28 to 38 carbon atoms, with a melting point of 75° C., manufactured by Nippon Seiro Co., Ltd.) (9 parts by mass) were dissolved at 120° C. After this, while they were stirred, morpholine (5 parts by mass) was added thereto. Then, hot water of 90° C. was dropped thereto in an amount that would result in a solid content of 30% by mass to form an oil-in-water emulsion. After this, the emulsion was cooled to thereby obtain an ester wax aqueous emulsion having a solid content of 30% by mass.

General Formula (1)

In General Formula (1) above, $R^1$ represents an alkyl group having 28 to 38 carbon atoms.

The average particle diameter of the obtained ester wax aqueous emulsion measured with a laser diffraction/scattering particle size distribution analyzer ("LA-920" manufactured by Horiba, Ltd.) was 0.4 μm.

Next, the obtained ester wax aqueous emulsion (with a solid content of 30% by mass) (100 parts by mass), and a carbon black water dispersion (FUJI SP BLACK 8625 manufactured by Fuji Pigment Co., Ltd., with a solid content of 30% by mass) (2 parts by mass) were mixed with each other, to thereby produce a flow path wall forming layer coating liquid.

<Production of Transfer Member for Flow Path Wall Formation>

The back layer coating liquid was applied over one side of a polyester film having an average thickness of 25 μm (LUMIRROR F65 manufactured by Toray Industries, Inc.) as a support member, and dried at 80° C. for 10 seconds, to thereby form a back layer having an average thickness of 0.02 μm.

Next, a releasing layer coating liquid was applied over a side of the polyester film opposite to the side thereof over which the back layer was formed, and dried at 40° C. for 10 seconds, to thereby form a releasing layer having an average thickness of 1.5 μm.

Next, the flow path wall forming layer coating liquid was applied over the releasing layer, and dried at 70° C. for 10 seconds, to thereby form a flow path wall forming layer having an average thickness of 100 μm. IN this way, a transfer member for flow path wall formation of Example 1 was produced.

<<Production of Hydrophilic Porous Base Member having Hydrophobic Substrate>

A polyester-based hot-melt adhesive (ALONMELT PES375S40 manufactured by Toagosei Co., Ltd.) as a thermoplastic material, was heated to 190° C., and then applied over a PET film (LUMIRROR S10 manufactured by Toray Industries, Inc., with a thickness of 50 μm) with a roll coater to have a thickness of 50 μm above the PET film, to thereby form an adhesive layer. The obtained applied product was kept stationary for 2 hours or longer. After this, a membrane filter made of PVDF (SVLP04700 manufactured by Merck Millipore Corporation, with a hydrophilic porous layer thickness of 125 μn, and a voidage of 70%) was overlapped with the adhesive layer side, and a load of 1 kgf/cm² was applied to them at 150° C. for 10 seconds, to thereby obtain a hydrophilic porous base member having a hydrophobic substrate.

<Formation of Flow Path Wall>

Figure 6:
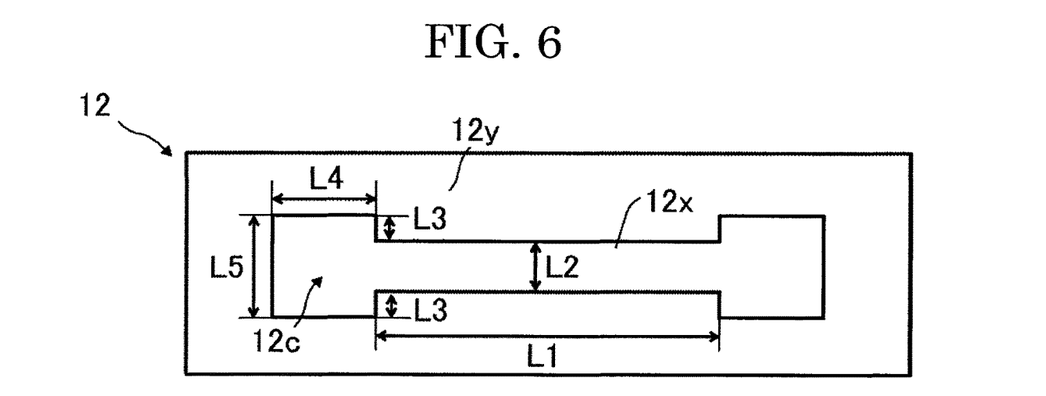
FIG. 6 is a plan view of a flow path member.

The produced transfer member for flow path wall formation and the hydrophilic porous layer side of the hydrophilic porous base member having the hydrophobic substrate were faced and overlapped with each other. After this, with a thermal transfer printer described above, thermal transfer was performed under pattern formation conditions described below, to thereby form a flow path wall having a shape shown in FIG. 6. After this, the flow path member and the transfer member for flow path wall formation were faced and overlapped with each other. After this, the barrier member 13 was formed with the thermal transfer printer, to thereby fabricate a testing device shown in FIG. 7. The lengths L1 to L5 in FIG. 6 are as follows.

L1: 40 mm
L2: 5 mm
L3: 2 mm
L4: 9 mm
L5: 9 mm

For the formation of the flow path wall in the hydrophilic porous base member, printing evaluation was performed by constructing an evaluation system with a thermal head having a head density of 300 dpi (manufactured by TDK Corporation), at a printing speed of 16.9 mm/sec, and with a printing energy of 0.81 mJ/dot.

For the formation of the barrier member 13, printing evaluation was performed by constructing the same evaluation system as described above, except that the printing energy was changed to 0.28 mJ/dot.

<Formation of Detection Region by Thermal Transfer>

The transfer member for reagent composition formation and a side of the testing device having the flow path wall were faced and overlapped with each other. After this, with the same thermal transfer printer as described above, thermal transfer was performed under pattern formation conditions described below. In this way, a reagent pattern having a thickness of 10 μm was formed in the reaction field R4 shown in FIG. 7, to thereby obtain a testing device of Example 1.

For the placement of the reagent composition, printing was performed by constructing an evaluation system with a thermal head having a head density of 300 dpi (manufactured by TDK Corporation), at a printing speed of 16.9 mm/sec, and with a printing energy of 0.28 mJ/dot.

(Evaluation of Line Visibility)

A clear and colorless 1% NaOH solution (35 μL) was dropped into the dropping region 12c of the testing device fabricated as above, and the degree of bleeding of the detection region that appeared in the reaction field R4 was observed visually. The degree of bleeding of the line (signal) was evaluated based on the evaluation criteria below. The result is shown in Table 1.

A: No bleeding was observed, and the line was clear.
B: Slight bleeding of the line was observed.
C: Bleeding of the line was observed, but judgment was narrowly possible.
D: Bleeding was serious, and judgment was impossible.

Example 2

<Production of Transfer Member for Reagent Composition Formation>
—Preparation of Reagent Composition Forming Layer Coating Liquid 1 (Test Line)—

Polyvinyl pyrrolidone (10 parts by mass), an anti-human IgG antibody (I1886 manufactured by Sigma-Aldrich Co., LLC., 4.7 mg/mL) (10 parts by mass) were dissolved and dispersed at room temperature (25° C.), to thereby produce a reagent composition forming layer coating liquid 1.
—Preparation of Reagent Composition Forming Layer Coating Liquid 2 (Control Line)—

Polyvinyl pyrrolidone (5259-100GM manufactured by Merck Millipore Corporation) (10 parts by mass), and human IgG (12511-10MG manufactured by Sigma-Aldrich Co., LLC., 4.8 mg/mL) (10 parts by mass) were dissolved and dispersed at room temperature (25° C.), to thereby produce a reagent composition forming layer coating liquid 2.

The back layer coating liquid described above was applied over one side of a polyester film having an average thickness of 4.5 μm (LUMIRROR F57 manufactured by Toray Industries, Inc.) as a support member, and dried at 80° C. for 10 seconds, to thereby form a back layer having an average thickness of 0.02 μm.

Next, the reagent composition forming layer coating liquid 1 was applied over a side of the polyester film opposite to the side thereof over which the back layer was formed, and dried at room temperature for 60 minutes, to thereby form a reagent composition forming layer having an average thickness of 10 μm. In this way, a transfer member for reagent composition formation 1 was produced. In the same manner, the reagent composition forming layer coating liquid 2 was applied over a side of a polyester film opposite to a side thereof over which a back layer was formed, and dried at room temperature for 60 minutes, to thereby form a reagent composition forming layer having an average thickness of 10 μm. In this way, a transfer member for reagent composition formation 2 was produced.

<Preparation of Flow Path Wall Forming Layer Coating Liquid>

An ester wax (WE-11 manufactured by NOF Corporation, with a melting start temperature of 65° C.) (100 parts by mass), montanic acid (product name: LUWAX-E manufactured by BASF Corporation, with a melting point of 76° C.) (2 parts by mass), and a long-chain alcohol represented by General Formula (1) below (where $R^1$ was an alkyl group having 28 to 38 carbon atoms, with a melting point of 75° C., manufactured by Nippon Seiro Co., Ltd.) (9 parts by mass) were dissolved at 120° C. After this, while they were stirred, morpholine (5 parts by mass) was added thereto. Then hot water of 90° C. was dropped thereto in an amount that would result in a solid content of 30% by mass to form an oil-in-water emulsion. After this, the emulsion was cooled to thereby obtain an ester wax aqueous emulsion having a solid content of 30% by mass.

General Formula (1)

In General Formula (1), $R^1$ represents an alkyl group having 28 to 38 carbon atoms.

The average particle diameter of the obtained ester wax aqueous emulsion measured with a laser diffraction/scattering particle size distribution analyzer ("LA-920" manufactured by Horiba, Ltd.) was 0.4 μm.

Next, the obtained ester wax aqueous emulsion (with a solid content of 30% by mass) (100 parts by mass), and a carbon black water dispersion (FUJI SP BLACK 8625 manufactured by Fuji Pigment Co., Ltd., with a solid content of 30% by mass) (2 parts by mass) were mixed with each other, to thereby produce a flow path wall forming layer coating liquid.

<Preparation of Releasing Layer Coating Liquid>

A polyethylene wax (POLYWAX 1000 manufactured by Toyo ADL Corporation, with a melting point of 99° C., and a needle penetration of 2 at 25° C.) (14 parts by mass), an ethylene/vinyl acetate copolymer (EV-150 manufactured by Du Pont-Mitsui Polychemicals Co., Ltd., with a weight average molecular weight of 2,100, and VAc of 21%) (6 parts by mass), toluene (60 parts by mass), and methyl ethyl ketone (20 parts by mass) were dispersed until the average particle diameter became 2.5 μm, to thereby obtain a releasing layer coating liquid.

<Preparation of Back Layer Coating Liquid>

An emulsion of a silicone-based rubber (KS779H manufactured by Shin-Etsu Chemical Co., Ltd., with a solid content of 30% by mass) (16.8 parts by mass), a chloroplatinic acid catalyst (0.2 parts by mass), and toluene (83 parts by mass) were mixed, to thereby obtain a back layer coating liquid.

<Production of Transfer Member for Flow Path Wall Formation>

The back layer coating liquid was applied over one side of a polyester film having an average thickness of 25 μm (LUMIRROR F65 manufactured by Toray Industries, Inc.) as a support member, and dried at 80° C. for 10 seconds, to thereby form a back layer having an average thickness of 0.02 μm. Then, the releasing layer coating liquid was applied over a side of the polyester film opposite to the side thereof over which the back layer was formed, and dried at 40° C. for 10 seconds, to thereby form a releasing layer having an average thickness of 1.5 μm.

Next, the flow path wall forming layer coating liquid was applied over the releasing layer, and dried at 70° C. for 10 seconds, to thereby form a flow path wall forming layer having an average thickness of 100 μm. In this way, a transfer member for flow path wall formation of Example 2 was produced.

<Production of Hydrophilic Porous Base Member having Hydrophobic Substrate>

A polyester-based hot-melt adhesive (ALONMELT PES375S40 manufactured by Toagosei Co., Ltd.), as a thermoplastic resin, was heated to 190° C., and then applied over a PET film (LUMIRROR S10 manufactured by Toray Industries, Inc., 50 μm) with a roll coater to have a thickness of 50 μm above the PET film, to thereby form an adhesive layer. The applied product was kept stationary for 2 hours or longer. After this, a nitrocellulose membrane filter (HI-FLOW PLUS HF135UBXSS manufactured by Merck Millipore Corporation, with a thickness of 135 μm, and a voidage of 70%) was overlapped with the adhesive layer side, and a load of 1 kgf/cm$^2$ was applied to them at 150° C., to thereby obtain a hydrophilic porous base member having a hydrophobic substrate. A blocking treatment described below was applied to the substrate.

[Blocking Treatment]

The nitrocellulose membrane filter was immersed in a blocking agent (a BSA-containing PBS solution (with pH of 7.4), P3688-10PAK, manufactured by Sigma-Aldrich Co., LLC.), and shaken gently for 20 minutes. After this, any excess moisture on the surface of the filter was sucked away, and the filter was dried at room temperature for 1 hour.

<Formation of Flow Path Wall by Thermal Transfer>

Figure 8:
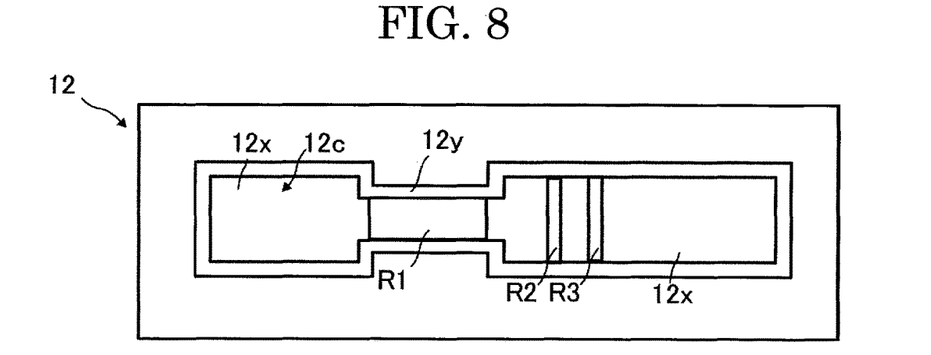
FIG. 8 is a plan view of a flow path member.

Next, a flow path wall was formed in the blocking treatment-applied substrate in the same manner as in Example 1, except that a flow path wall 12y having a width of 700 μm shown in FIG. 8 was formed instead of forming the flow path wall 12y having the shape shown in FIG. 6.

For the formation of the flow path wall 12y filled in the hydrophilic porous base member, printing evaluation was performed by constructing an evaluation system with a thermal head having a head density of 300 dpi (manufactured by TDK Corporation), at a printing speed of 16.9 mm/sec, and with a printing energy of 0.81 mJ/dot.

<Placement of Reagent Composition by Thermal Transfer>

The transfer member for reagent composition formation 1and a side of the flow path member having the flow path wall were faced and overlapped with each other. After this, with the same thermal transfer printer as described above, thermal transfer was performed under pattern formation conditions described below, to thereby form as a test line, a reagent pattern having a thickness of 10 μm and a line width of 1 mm in the reaction field R2 shown in FIG. 8. Under the same conditions, the transfer member for reagent composition formation 2 was thermally transferred, to thereby form as a control line, a reagent pattern having a thickness of 10 μm and a line width of 1 mm in the reaction field R3.

For the formation of the reagent patterns, printing was performed by constructing an evaluation system with a thermal head having a head density of 300 dpi (manufactured by TDK Corporation), at a printing speed of 16.9 mm/sec, and with a printing energy of 0.28 mJ/dot.

Next, as a gold colloid-labeled antibody, a gold colloid-labeled anti-human IgG antibody (Gold 40 nm, OD=15, manufactured by Bioassay Works, LLC) (5 μL) was applied in the reaction field R1.

Then, the transfer member for flow path wall formation was again faced and overlapped with the flow path member having the shape shown in FIG. 8. After this, a barrier member 13 was formed with a thermal transfer printer under the same printing conditions as in Example 1, to thereby obtain an immunochromatography assay (testing device) shown in FIG. 9.

Figure 9:
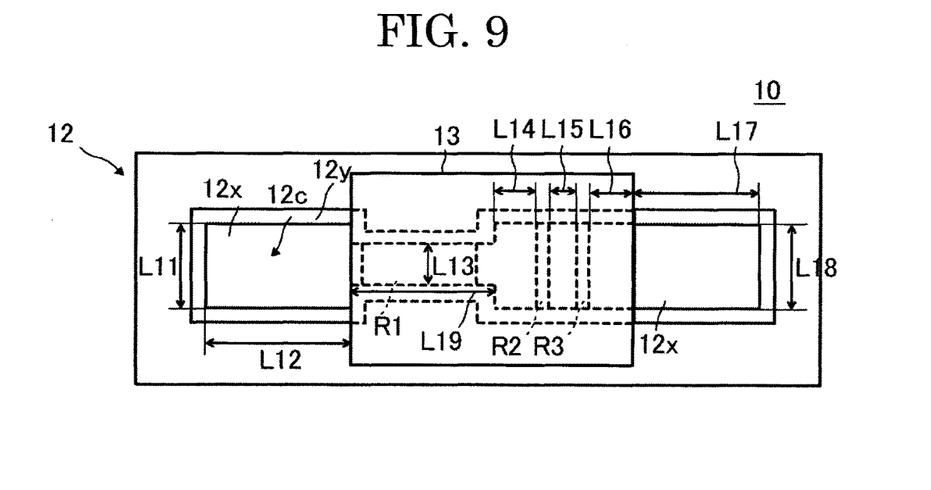
FIG. 9 is a plan view of a testing device.

The lengths L11 to L19 in FIG. 9 are as follows.
L11: 5 mm
L12: 17 mm
L13: 3 mm
L14: 5 mm
L15: 5 mm
L16: 5 mm
L17: 17 mm
L18: 5 mm
L19: 17 mm After this, a human IgG 2 mg/ml solution (50 μL) diluted with purified water was dropped into the dropping region 12c. As a result, it was observed that the solution penetrated through the flow path by a capillary action, and lines having a width of 1 mm appeared in the reaction field R2 (test line) and the reaction field R3 (control line). From this fact, it was confirmed that the testing device functioned as a biochemical sensor.

(Evaluation of Line Visibility)

Bleeding of the lines having a width of 1 mm that appeared in the reaction field R2 (test line) and the reaction field R3 (control line) of the immunochromatography assay fabricated as above was evaluated based on the evaluation criteria below. The result is shown in Table 1.

A: No bleeding was observed, and the line was clear.
B: Slight bleeding of the line was observed.
C: Bleeding of the line was observed, but judgment was narrowly possible.
D: Bleeding was serious, and judgment was impossible.

Examples 3 to 6

Immunochromatography assays were fabricated and evaluated in the same manner as in Example 2 including the amount of use, except that polyvinyl pyrrolidone (5259-100GM manufactured by Merck Millipore Corporation), as a hydrophilic resin of Example 2, was changed to hydrophilic resins described in the field of Examples 3 to 6 of Table 1 respectively.

An immunochromatography assay of Example 7 was fabricated and evaluated in the same manner as in Example 2 including the amount of use, except that the membrane filter made of PVDF was changed to a membrane filter made of hydrophilized PTFE (JCWP14225 manufactured by Merck Millipore Corporation, with a thickness of 100 μm, and a voidage of 70%).

However, a blocking treatment was not applied in Example 7.

The followings were used as the hydrophilic resins of the respective Examples.

(Example 3) Polyvinyl alcohol (PVA) (KURARAY POVAL CP-1210 manufactured by Kuraray Co., Ltd.)

(Example 4) Polyvinyl butyral (PVB) (ESLEC KW-10 manufactured by Sekisui Chemical Co., Ltd.)

(Example 5) Polyethylene oxide (PEO) (ALKOX L-6 manufactured by Meisei Chemical Works, Ltd.)

(Example 6) Polyethylene glycol (PEG) (PEG-6000J manufactured by Lion Corporation).

The results are shown in Table 1.

Comparative Example 1

—Preparation of Ultraviolet Curable Ink—

A mixture of octadecyl acrylate, as a photo-radical-polymerizable monomer, and 1,10-bis(acryloyloxy)decane (DDA), as a photo-radical-polymerizable oligomer, at a ratio of 7:3 (on a mass basis) was prepared. Benzyl dimethyl ketal (BDK), as a photo polymerization initiator was dissolved in the mixture at a final concentration of 15% by mass, to thereby obtain an ultraviolet curable ink.

The ultraviolet curable ink prepared as above was filled in ink cartridges of a piezo inkjet printer (PX-101) commercially available from Epson Corporation, and flow path printing was performed with this printer. The printed flow path had a shape of two squares with a length of 9 mm on each side being linked with each other by a flow path having a length of 40 mm and a width of 5 mm, as in FIG. 6. One of the squares was the position to which to drop the analyte, and the other square was the reaction field. The ultraviolet curable ink was filled in all cartridges, and printing was performed under a setting of monochrome printing, based on a pattern drawn with drawing software. The same membrane filter as in Example 1 was used as a sheet.

—Preparation of Reagent Ink—

(i) A 1.94% by mass bromthymol blue (BTB) solution as a pH indicator was prepared in an amount of 1,246 (4).

(ii) To clear up pH responsivity, the pH indicator of (0 and a 0.1 M NaOH solution were mixed at 10:36.3 (µL). It was confirmed that the color of the solution turned green.

(iii) The BTB solution of (i), glycerin, 2-propanol, and MILLI-Q WATER were mixed and prepared at a ratio of 1,246:500:1,500:1,754 (µL). MILLI-Q WATER was ultrapure water produced by using MILLI-Q in an ultrapure water system manufactured by Millipore Corporation.

(iv) The prepared reagent ink was subjected to ultrafiltration to remove impurities, filled in the ink cartridges of the same inkjet printer as described above, printed at one of the squares of the pattern described above, and dried. In this way, a testing device of Comparative Example 1 was fabricated.

(Evaluation of Line Visibility)

A clear and colorless 1% NaOH solution (35 µL) was dropped into the dropping region of the testing device fabricated as above, and the degree of bleeding of the detection region that appeared in the reaction field at the square formed in (iv) was observed visually. The degree of bleeding of the line (signal) was evaluated based on the evaluation criteria below. The result is shown in Table 2.

A: No bleeding was observed, and the line was clear.

B: Slight bleeding of the line was observed.

C: Bleeding of the line was observed, but judgment was narrowly possible.

D: Bleeding was serious, and judgment was impossible.

Comparative Example 2

—Preparation of Ultraviolet Curable Ink—

A mixture of octadecyl acrylate, as a photo-radical-polymerizable monomer, and 1,10-bis(acryloyloxy)decane (DDA), as a photo-radical-polymerizable oligomer, at a ratio of 7:3 (on a mass basis) was prepared. Benzyl dimethyl ketal (BDK), as a photo polymerization initiator was dissolved in the mixture at a final concentration of 15% by mass, to thereby obtain an ultraviolet curable ink.

[Blocking Treatment]

The same membrane filter as in Example 2 was immersed in a blocking agent (a BSA-containing PBS solution (with a pH of 7.4), P3688-10PAK manufactured by Sigma-Aldrich Co., LLC.), and shaken gently for 20 minutes. After this, any excess moisture on the surface of the filter was sucked away, and the filter was dried at room temperature.

The ultraviolet curable ink prepared as above was filled in ink cartridges of a piezo inkjet printer (PX-101) commercially available from Epson Corporation, and flow path printing was performed with this printer. The printed flow path had the same pattern as in FIG. 8. One of the rectangles was the position from which to drop the analyte, and the other rectangle was the reaction field. The ultraviolet curable ink was filled in all cartridges, and printing was performed under a setting of monochrome printing, based on a pattern drawn with drawing software. The blocking treatment-applied membrane filter was used as a porous base member.

—Preparation of Reagent Ink—

As a reagent ink 1, an anti-human IgG antibody (4.7 mg/mL, I1886, manufactured by Sigma-Aldrich Co., LLC.), and MILLI-Q water were mixed and prepared at a ratio of 1,000:1,000 (µL). Further, as a reagent ink 2, human-IgG (4.8 mg/mL I2511-10MG, manufactured by Sigma-Aldrich Co., LLC.), and MILLI-Q water were mixed and prepared at a ratio of 1,000:1,000 (µL) in the same manner. The prepared reagent ink 1 was filled in the ink cartridges of the same inkjet printer as in Comparative Example 1, and printed as a test line at the same position as the reaction field R2 of FIG. 8 to have a width of 1 mm. Further, in the same manner, the prepared reagent ink 2 was printed as a control line at the same position as the reaction field R3 of FIG. 8 to have a width of 1 mm. After this, the inks were dried at room temperature for 30 minutes to 60 minutes.

Next, as a gold colloid-labeled antibody, gold colloid-labeled anti-human IgG (Gold 40 nm, OD=15, manufactured by Bioassay Works, LLC) (5 µL) was applied at the same position as the reaction field R1 of FIG. 8 with a micropipette.

After this, a human IgG 2 mg/ml solution (50 µL) diluted with purified water was dropped into the dropping region. As a result, it was observed that the solution penetrated through the flow path by a capillary action, and lines having a width of 1 mm vaguely appeared at the test line and at the control line.

(Evaluation of Line Visibility)

Bleeding of the lines having a width of 1 mm that appeared in the reaction field R2 (test line) and the reaction field R3 (control line) of the immunochromatography assay fabricated as above was evaluated based on the evaluation criteria below. The result is shown in Table 2.

A: No bleeding was observed, and the line was clear.

B: Slight bleeding of the line was observed.

C: Bleeding of the line was observed, but judgment was narrowly possible.

D: Bleeding was serious, and judgment was impossible.

Comparative Example 31

An immunochromatography assay (testing device) was fabricated in the same manner as in Example 2, except that unlike in Example 2, an anti-human IgG antibody 4.7 mg/mL solution was applied with a micropipette in the reaction field R2 instead of thermally transferring the transfer member for reagent composition formation 1 and a human IgG 4.8 mg/mL solution was applied with a micropipette in the reaction field R3 instead of thermally transferring the transfer member for reagent composition formation 2, both to have a line shape having a width of 1 mm and a length of 5 mm, and then the applied solutions were dried at room temperature for 1 hour in a stationary state. Then, evaluation of the visibility of the detection lines was performed. The result is shown in Table 2.

TABLE 1

| No. | Reactive reagent | Hydrophilic resin | Base member | Visibility |
|---|---|---|---|---|
| Ex. 1 | BTB indicator | PVP | Membrane filter (PVDF) | A |
| Ex. 2 | Human IgG Anti-human IgG | PVP | Membrane filter (nitrocellulose) | A |
| Ex. 3 | Human IgG Anti-human IgG | PVA | Membrane filter (nitrocellulose) | A |
| Ex. 4 | Human IgG Anti-human IgG | PVB | Membrane filter (nitrocellulose) | A |
| Ex. 5 | Human IgG Anti-human IgG | PEO | Membrane filter (nitrocellulose) | B |
| Ex. 6 | Human IgG Anti-human IgG | PEG | Membrane filter (nitrocellulose) | B |
| Ex. 7 | Human IgG Anti-human IgG | PVP | Membrane filter (hydrophilized PTFE) | A |

TABLE 2

| No. | Reactive reagent | Application method | Base member | Visibility |
|---|---|---|---|---|
| Comp. Ex. 1 | BTB indicator | IJ | Membrane filter (PVDF) | D |
| Comp. Ex. 2 | Human IgG Anti-human IgG | IJ | Membrane filter (nitrocellulose) | D |
| Comp. Ex. 3 | Human IgG Anti-human IgG | Dispensing | Membrane filter (nitrocellulose) | C |

Aspects of the present invention are as follows, for example.

<1> A testing device, including:
   a flow path in which an analyte is flowed,
   wherein a composition containing a reagent reactive with the analyte and a lyophilic resin is placed at one position or a plurality of positions of the flow path.

<2> The testing device according to <1>,
   wherein the lyophilic resin is a thermoplastic resin.

<3> The testing device according to <1> or <2>,
   wherein the composition is fixed in the flow path.

<4> The testing device according to any one of <1> to <3>,
   wherein the reagent is a reagent that undergoes an antigen-antibody reaction.

<5> The testing device according to any one of <1> to <4>,
   wherein the reagent is a reagent that changes its hue due to a change in its structure.

<6> A transfer member for testing device fabrication, including:
   a reagent composition forming layer that contains a composition,
   wherein the composition contains a reagent for detecting an analyte, and a lyophilic resin, and
   wherein the lyophilic resin is a thermoplastic resin.

<7> A method for fabricating a testing device, including:
   bringing the reagent composition forming layer of the transfer member according to <6> and a porous material into contact with each other, and applying heat and pressure to the transfer member to thereby transfer the reagent composition forming layer onto the porous material.

<8> A testing method, including:
   supplying the analyte into the flow path of the testing device according to any one of <1> to <5>, and making a predetermined judgment based on a reaction between the analyte and the reagent placed in the flow path.

REFERENCE SIGNS LIST 10 testing device
11 base member
12 flow path member
12a, 12b pore
12c dropping region
12d absorbent region
12x porous portion
12y flow path wall
13 barrier member
14 absorbent member
100 transfer member for flow path wall formation
101 support member
102 releasing layer
103 back layer
112y flow path wall forming layer
200 transfer member for reagent composition formation
201 support member
202 releasing layer
203 back layer
213 reagent composition forming layer

The invention claimed is:

1. A testing device, comprising:
   a flow path for flowing an analyte upon application, wherein the flow path comprises a porous portion that is made up of a hydrophilic porous material which is not hydrophobized, and
   a composition that comprises a reagent reactive with the analyte and a lyophilic resin placed by thermal transfer printing at one position or a plurality of positions of the flow path,
   wherein the lyophilic resin is a hydrophilic, thermoplastic resin, and
   wherein the composition is fixed in the flow path.

2. The testing device of claim 1, wherein the reagent is a reagent that undergoes an antigen-antibody reaction.

3. The testing device of claim 1, further comprising a base, wherein the flow path is provided over the base.

4. The testing device of claim 3, wherein at least one side of the base is covered with a hydrophobic resin.

5. The testing device of claim 3, wherein a material of the base is at least one selected from the group consisting of polyvinyl chloride, polyethylene terephthalate, polypropylene, polystyrene, polyvinyl acetate, polycarbonate, polyacetal, modified polyphenyl ether, and polybutylene terephthalate.

6. The testing device of claim 3, wherein an average thickness of the base is from 0.01 mm to 0.5 mm.

7. The testing device of claim 1, wherein the flow path further comprises a flow path wall that is hydrophobized.

8. The testing device of claim 7, wherein the hydrophilic porous material has an average thickness from 0.01 mm to 0.3 mm.

9. The testing device of claim 1, wherein the composition is fixed in pores of the porous portion of the flow path.

* * * * *